United States Patent [19]

Carman

[11] Patent Number: 5,291,902

[45] Date of Patent: Mar. 8, 1994

[54] INCONTINENCE TREATMENT

[76] Inventor: Brent Carman, R.R. #1, Millarville, Alberta, T0L 1K0, Canada

[21] Appl. No.: 3,052

[22] Filed: Jan. 11, 1993

[51] Int. Cl.$^5$ .............................................. A61N 1/00
[52] U.S. Cl. ................................................... 607/138
[58] Field of Search .............. 128/733, 734, 774, 775, 128/778, 782, 784, 788

[56] References Cited

U.S. PATENT DOCUMENTS

| | | | |
|---|---|---|---|
| 3,236,240 | 2/1966 | Bradley . | |
| 3,628,538 | 12/1971 | Vincent et al. . | |
| 3,646,940 | 3/1972 | Timm et al. | 128/419 E |
| 3,650,276 | 3/1972 | Burghele et al. | 128/419 E |
| 3,667,477 | 6/1972 | Susset et al. | 128/419 E |
| 3,800,800 | 4/1974 | Garbe et al. | 128/408 |
| 3,870,051 | 3/1975 | Brindley | 128/422 |
| 3,933,147 | 1/1976 | Du Vall et al. | 128/788 |
| 4,102,344 | 7/1978 | Conway et al. | 128/419 E |
| 4,106,511 | 8/1978 | Erlandsson | 128/407 |
| 4,387,719 | 6/1983 | Plevnik et al. | 128/421 |
| 4,607,639 | 5/1986 | Tanagho et al. | 128/419 E |
| 4,688,575 | 8/1987 | Du Vall | 128/788 |
| 4,785,813 | 11/1988 | Petrofsky | 128/733 |
| 4,785,828 | 10/1988 | Maurer | 128/788 |
| 5,117,840 | 6/1992 | Brenman et al. | 128/788 |
| 5,199,443 | 4/1993 | Maurer et al. | 128/788 |

*Primary Examiner*—Max Hindenburg
*Attorney, Agent, or Firm*—Rogers & Scott

[57] ABSTRACT

A method of improving the pelvic floor muscle strength of a person in a manner to lessen urinary incontinence includes placing surface electrodes of electromyographic measuring apparatus on the perineum of the person, measuring with said apparatus the bladder controlling pelvic floor muscle strength of the person while the person is tensing the pelvic floor muscles in a urine stopping manner to obtain an EMG signal, and adjusting the threshold value of a portable electromyographic measuring unit to enable the person to repeat the measurement at different times to attempt to obtain better EMG signals in a urinary incontinence reducing sense. The portable unit gives an audible and/or visual indication when an EMG signal above the threshold value is achieved.

14 Claims, No Drawings

INCONTINENCE TREATMENT

This invention relates to the treatment of urinary incontinence.

Urinary incontinence is of course a well known medical problem and many attempts have been made to provide methods of treatment. However, none of the methods previously proposed have proved to be as successful as desired.

It is therefore an object of the invention to provide an improved method for treating urinary incontinence.

According to the invention, a method of improving the pelvic muscle strength of a person in a manner to lessen urinary incontinence comprises placing surface electrodes of electromyographic measuring apparatus on the perineum of the person, measuring with said apparatus the bladder controlling pelvic floor muscle strength of the person while the person is tensing the pelvic floor muscles in a urine stopping manner to obtain an EMG signal, and adjusting the threshold value of a portable electromyographic measuring unit to enable the person to repeat said measurement at different times to attempt to obtain better EMG signals in a urinary incontinence reducing sense, said portable unit giving an audible and/or visual indication when an EMG signal above said threshold value is achieved.

When the measurement has been made and the threshold value of the electromyographic unit has been appropriately adjusted by a professional, the person can perform specified physical exercises which are designed to improve pelvic muscle control in a manner to reduce urinary incontinence and then use the electromyographic unit provided to see if better EMG signals can be obtained, i.e. to see if the exercises are having a beneficial effect. In due course the person will again be checked by a professional and a further measurement made. The professional will then re-adjust the threshold value of the electromyographic unit to give the person a further incentive to continue the specified physical exercises.

The bladder controlling pelvic floor muscle strength may be measured while the person is at rest and not consciously tensing the pelvic muscles in a urine stopping manner to obtain a first EMG signal, while the person is tensing the pelvic floor muscles in a urine stopping manner for a short period of time to obtain a second EMG signal, and while the person is tensing the pelvic floor muscles in a urine stopping manner for a longer period of time to obtain a third EMG signal.

The threshold value of the portable electromyographic unit may be adjusted to a value which is from about 60 to about 80% of the best measurement while the person is tensing the pelvic floor muscles in a urine stopping manner.

The electrodes may be simply applied to the surface of the body, without implantation being necessary. In other words, the electrodes can be non-invasive. The skin need not be prepared with solvents or broken with needles.

The short period of time may be in the range of from about 2 to about 5 seconds, for example about 2 seconds. The longer period of time may be in the range of from about 10 to about 30 seconds, for example about 10 seconds.

The method may further include applying neuromuscular stimulation in the form of repeated applications of electrical pulses to the pelvic floor muscles to cause the muscles to repeatedly contract and relax and consequently grow and increase in strength to lessen urinary incontinence.

When stress incontinence is to be treated, the electrical pulses may have a peak current in the range of from about 10 to about 100 milliamps and a frequency in the range of from about 40 to about 60 Hertz and be applied in pulses lasting from about 5 to about 10 seconds with an interval between pulses in the range of from about 5 to about 10 seconds.

The electrical pulses may have a peak current of about 40 milliamps and a frequency of about 50 Hz and be applied as pulses lasting from about 5 seconds with an interval between pulses of from about 5 to about 10 seconds.

When urge incontinence is to be treated, the electrical pulses may have a peak current in the range from about 10 to pulses may have a peak current in the range from about 10 to about 100 milliamps and a frequency in the range of from about 10 to about 15 Hz and be applied as pulses lasting from about 5 to about 10 seconds with an interval between pulses of from about 5 to about 10 seconds.

The electrical pulses may have a peak current of about 40 milliamps and a frequency of about 13 Hz and be applied as pulses lasting for about 5 seconds with an interval between pulses of from about 5 to about 10 seconds.

When treating a person with urinary incontinence in accordance with the invention, the initial treatment session involves the taking of baseline electromyographic measurements of the strength of the muscles of the pelvic floor which control urination. Suitable equipment for this purpose is for example the Speakeasy MC (®) equipment which is primarily intended for use in speech therapy. Two surface electrodes are placed on the perineum of the person and readings of muscle strength in microvolts are taken while the person is at rest, while the person is exerting maximum pelvic muscle contraction in a urine stopping manner for a short period of time, and while the person is exerting maximum pelvic muscle contraction in a urine stopping manner for a longer period of time. For example, the short period of time may be about 2 seconds and the longer period of time may be about 10 seconds.

The person is then taught appropriate exercises such as those known to a person skilled in the art or other suitable exercises to strengthen the appropriate pelvic muscles, with emphasis on the short hold time and the longer hold time mentioned above. The person is then given a portable electromyographic feedback unit for his/her personal use so that the person can practice the exercises at home or elsewhere and seek to improve on the baseline measurements. Suitable equipment for this purpose is the Speakeasy TH (®) equipment which again is primarily intended for use in speech therapy.

Before giving the unit to the person, the threshold value of the unit is adjusted by a professional to a value related to the person's baseline measurements, for example from about 60 to about 80% of the person's best effort during long hold. The settings for such a unit are typically from about 1 to about 10 microvolts. Thus, the person receives audio and/or visual feedback from the unit and is thereby encouraged to increase the feedback output by producing stronger contractions.

In addition to the biofeedback exercises, the person is put on a voiding, i.e. bladder emptying, regimen which is regularly adjusted by the professional, for example on a weekly basis. An appropriately set timer may be provided for this purpose. Every time the timer alarm sounds, the person must go to the toilet and try to void.

The person may also be given neuromuscular stimulation in the form of repeated applications of electrical pulses to the appropriate pelvic floor muscles to cause them to repeatedly contract and relax. Suitable equipment for this purpose is the Respond Select equipment manufactured by Medtronic Nortech and intended for use in rebuilding muscles of the shoulder, knee, hip and hand following disease, surgery or injury. Such stimulation causes muscle growth and increased muscle strength.

For stress incontinence, namely incontinence caused by various forms of physical activity, the pulses may have a frequency in the range of from about 40 to about 60 Hz, preferably about 50 Hz, and last for about 5 seconds with an off interval of about 10 seconds, increasing to lasting for about 5 seconds with an off interval of about 5 seconds, the session lasting from about 15 to about 30 minutes. There may be several such sessions per day.

It has been found that a frequency of about 50 Hz is preferable for stress incontinence in that it has been found to be the best frequency to enhance the pelvic floor musculature and improve urethal closure without rapid muscle fatigue. In other words, such a frequency automates pelvic floor muscle exercises. It has been found that muscle contraction occurs at or above about 40 Hz and that frequencies somewhat above about 50 Hz cause muscle fatigue. Accordingly therefore, about 50 Hz is the prefered neuromuscular stimulation frequency for treating stress incontinence.

For urge incontinence, namely incontinence caused by a full or nearly full bladder, pulse frequency may be from about 10 to about 15 Hz, preferably about 13 Hz, with the pulses being applied as for stress incontinence.

Urge incontinence is treated with a lower frequency because it has been found that bladder inhibition occurs with lower frequencies. However, at frequencies below about 10 Hz, some people experience discomfort or pain. Accordingly therefore, it has been found that a frequency of from about 13 to about 15 Hz is preferable for treating urge incontinence in that this produces pain-free, low frequency stimulation which results in bladder inhibition by reflexive mechanisms.

It should be pointed out that the intensity of the neuromuscular stimulation is not an exact science but depends on the individual person's reaction to stimulii. The intensity must be sufficient to cause muscle contraction. It has been found that an intensity of about 40 milliamps is usually appropriate for stress incontinence and urge incontinence, but this may not be true in every case. The intensity may in fact be varied in the range of from about 10 to about 100 milliamps.

Two specific examples of treatment will now be given. The first example is of a person with urge incontinence and the second example is of a person with stress incontinence. In each example, EMG signal readings and other information are given for an initial session and for the subsequent second, third, fourth and fifth sessions which occurred at weekly intervals. It will be noted that the EMG signal readings are taken when the person is sitting and when the person is standing, and that each reading is taken twice to avoid errors caused by spurious readings.

COMMENTS ON EXAMPLE 1 (URGE INCONTINENCE)

The dramatic improvement by the fifth session is readily apparent. In some cases, as in this example, it is necessary also to measure abdominal muscle activity and to condition the person to lessen such muscle contraction when contracting the pelvic floor muscles. In this example, no neuromuscular stimulation was required.

COMMENTS ON EXAMPLE 2 (STRESS INCONTINENCE)

Again, the dramatic improvement by the fifth session is readily apparent. In this example, it was not necessary to monitor abdominal muscle activity. However, neuromuscular stimulation was applied.

The advantages of the invention will be readily apparent to a person skilled in the art from the foregoing description, the scope of the invention being defined in the appended claims.

| EXAMPLE 1 (URGE INCONTINENCE) | | |
|---|---|---|
| | EMG SIGNAL (uV) | |
| | Sitting | Standing |
| FIRST SESSION | | |
| 1. Person at rest | | |
| Pelvic floor | 1.11/1.20 | 1.3/1.31 |
| Abdomen | 2.0/2.11 | 1.9/2.20 |
| 2. Short Hold (2 sec.) | | |
| Pelvic floor | 2.30/1.9 | 2.21/2.16 |
| Abdomen | 5.7/5.0 | 6.11/6.01 |
| 3. Long Hold (10 sec.) | | |
| Pelvic Floor | 1.96/1.90 | 2.01/2.70 |
| Abdomen | 4.33/4.71 | 5.31/5.44 |
| 4. Suggested voiding interval | 20 mins | |
| 5. EMG Home Unit Setting | 1.5 uV. | |
| 6. Neurostimulation Unit Setting | N/A | |
| 7. Number of accidents per day | More than 2 | |
| SECOND SESSION | | |
| 1. Person at rest | | |
| Pelvic floor | .97/1.09 | 1.19/1.17 |
| Abdomen | 1.35/1.01 | 2.00/2.10 |
| 2. Short Hold (2 sec.) | | |
| Pelvic floor | 3.96/2.91 | 3.01/3.20 |
| Abdomen | 1.55/1.73 | 1.96/1.80 |
| 3. Long Hold (10 sec.) | | |
| Pelvic Floor | 3.44/3.10 | 3.27/3.49 |
| Abdomen | 1.40/1.75 | 1.90/1.91 |
| 4. Suggested voiding interval | 45 mins | |
| 5. EMG Home Unit Setting | 2.4 uV. | |
| 6. Neurostimulation Unit Setting | N/A | |
| THIRD SESSION | | |
| 1. Person at rest | | |
| Pelvic floor | .88/.98 | 1.12/1.20 |
| Abdomen | N/A | |
| 2. Short Hold (2 sec.) | | |
| Pelvic floor | 4.14/4.33 | 4.56/4.9 |
| Abdomen | N/A | |
| 3. Long Hold (10 sec.) | | |
| Pelvic Floor | 4.01/4.09 | 4.0/3.97 |
| Abdomen | N/A | |
| 4. Suggested voiding interval | 60 mins | |
| 5. EMG Home Unit Setting | 3 uV. | |
| 6. Neurostimulation Unit Setting | N/A | |
| 7. Number of accidents per day | 1 | |
| FOURTH SESSION | | |
| 1. Person at rest | | |
| Pelvic floor | .80/.87 | 1.0/.93 |
| Abdomen | N/A | |
| 2. Short Hold (2 sec.) | | |
| Pelvic floor | 6.11/5.87 | 5.9/6.02 |
| Abdomen | N/A | |

EXAMPLE 1 (URGE INCONTINENCE)

| | EMG SIGNAL (uV) | |
|---|---|---|
| | Sitting | Standing |
| 3. Long Hold (10 sec.) | | |
| Pelvic Floor | 5.44/5.9 | 4.9/5.22 |
| Abdomen | N/A | |
| 4. Suggested voiding interval | 90 mins | |
| 5. EMG Home Unit Setting | 4.1 uV. | |
| 6. Neurostimulation Unit Setting | N/A | |
| 7. Number of accidents per day | 0 | |
| FIFTH SESSION | | |
| 1. Person at rest | | |
| Pelvic floor | .81/.89 | 1.02/.95 |
| Abdomen | N/A | |
| 2. Short Hold (2 sec.) | | |
| Pelvic floor | 10.04/9.77 | 10.6/11.01 |
| Abdomen | N/A | |
| 3. Long Hold (10 sec.) | | |
| Pelvic Floor | 9.87/9.8 | 9.9/10.12 |
| Abdomen | N/A | |
| 4. Suggested voiding interval | 120 mins | |
| 5. EMG Home Unit Setting | N/A | |
| 6. Neurostimulation Unit Setting | N/A | |
| 7. Number of accidents per day | 0 | |

EXAMPLE 2 (STRESS INCONTINENCE)

| | EMG SIGNAL (uV) | |
|---|---|---|
| | Sitting | Standing |
| FIRST SESSION | | |
| 1. Person at rest | | |
| Pelvic floor | .89/1.07 | .99/1.21 |
| Abdomen | N/A | |
| 2. Short Hold (2 sec.) | | |
| Pelvic floor | 2.11/1.80 | 2.67/2.57 |
| Abdomen | N/A | |
| 3. Long Hold (10 sec.) | | |
| Pelvic Floor | 1.88/1.57 | 2.01/1.98 |
| Abdomen | N/A | |
| 4. Suggested voiding interval | 30 mins | |
| 5. EMG Home Unit Setting | 1.2 uV. | |
| 6. Neurostimulation Unit Setting | 40 mA | |
| 7. Number of accidents per day | more than 2 | |
| SECOND SESSION | | |
| 1. Person at rest | | |
| Pelvic floor | .99/.89 | 1.02/1.11 |
| Abdomen | N/A | |
| Short Hold (2 sec.) | | |
| Pelvic floor | 2.99/3.01 | 3.54/3.77 |
| Abdomen | N/A | |
| 3. Long Hold (10 sec.) | | |
| Pelvic Floor | 2.50/2.93 | 3.60/3.89 |
| Abdomen | N/A | |
| 4. Suggested voiding interval | 45 mins | |
| 5. EMG Home Unit Setting | 2.25 uV. | |
| 6. Neurostimulation Unit Setting | 40 mA | |
| 7. Number of accidents per day | 3 | |
| THIRD SESSION | | |
| 1. Person at rest | | |
| Pelvic floor | .91/.90 | .99/1.04 |
| Abdomen | N/A | |
| 2. Short Hold (2 sec.) | | |
| Pelvic floor | 3.03/4.11 | 4.01/3.90 |
| Abdomen | N/A | |
| 3. Long Hold (10 sec.) | | |
| Pelvic Floor | 3.27/3.98 | 4.21/4.01 |
| Abdomen | N/A | |
| 4. Suggested voiding interval | 60 mins | |
| 5. EMG Home Unit Setting | 3 uV. | |
| 6. Neurostimulation Unit Setting | Discontinued | |
| 7. Number of accidents per day | 1 | |
| FOURTH SESSION | | |
| 1. Person at rest | | |
| Pelvic floor | .77/1.01 | .99/1.11 |
| Abdomen | N/A | |
| 2. Short Hold (2 sec.) | | |
| Pelvic floor | 5.11/5.78 | 6.02/6.11 |
| Abdomen | N/A | |
| 3. Long Hold (10 sec.) | | |
| Pelvic Floor | 4.97/5.0 | 5.1/5.5 |
| Abdomen | N/A | |
| 4. Suggested voiding interval | 90 mins | |
| 5. EMG Home Unit Setting | 4.5 uV. | |
| 6. Neurostimulation Unit Setting | N/A | |
| 7. Number of accidents per day | 0 | |
| FIFTH SESSION | | |
| 1. Person at rest | | |
| Pelvic floor | 1.02/1.09 | 1.20/1.11 |
| Abdomen | N/A | |
| 2. Short Hold (2 sec.) | | |
| Pelvic floor | 8.71/9.21 | 10.11/10.60 |
| Abdomen | N/A | |
| 3. Long Hold (10 sec.) | | |
| Pelvic Floor | 8.90/9.01 | 10.02/10.90 |
| Abdomen | N/A | |
| 4. Suggested voiding interval | 110 mins | |
| 5. EMG Home Unit Setting | N/A | |
| 6. Neurostimulation Unit Setting | | |
| 7. Number of accidents per day | 0 | |

I claim:

1. A method of improving the pelvic floor muscle strength of a person in a manner to lessen urinary incontinence comprising;

placing surface electrodes of electromyographic measuring apparatus on the perineum of the person, measuring with said apparatus the bladder controlling pelvic floor muscle strength of the person while the person is tensing the pelvic floor muscles in a urine stopping manner to obtain an EMG signal, and adjusting the threshold value of a portable electromyographic measuring unit to enable the person to repeat said measurement at different times to attempt to obtain better EMG signals in a urinary incontinence reducing sense, said portable unit giving an audible and/or visual indication when an EMG signal above said threshold value is achieved.

2. A method according to claim 1, comprising;

measuring with said apparatus the bladder controlling pelvic floor muscle strength of the person while the person is at rest and not consciously tensing the pelvic muscles in a urine stopping manner to obtain a first EMG signal, while the person is tensing the pelvic floor muscles in a urine stopping manner for a short period of time to obtain a second EMG signal, and while the person is tensing the pelvic floor muscles in a urine stopping manner for a longer period of time to obtain a third EMG signal.

3. A method according to claim 2 wherein the threshold value of the portable electromyographic measuring unit is adjusted to a value which is from about 60 to about 80% of the best measurement while the person is tensing the pelvic floor muscles in a urine stopping manner.

4. A method according to claim 2 wherein the short period of time is in the range from about 2 to about 5 seconds.

5. A method according to claim 4 wherein the short period of time is about 2 seconds.

6. A method according to claim 2 wherein the longer period of time is in the range of from about 10 to about 30 seconds.

7. A method according to claim 6 wherein the longer period of time is about 10 seconds.

8. A method according to claim 2 wherein the short period of time is in the range of from about 2 to about 5 seconds and the longer period of time is in the range of from about 10 to about 30 seconds.

9. A method according to claim 8 wherein the short period of time is about 2 seconds and the longer period of time is about 10 seconds.

10. A method according to claim 1 further including; repeatedly applying neuromuscular stimulation in the form of electrical pulses to the pelvic floor muscles to cause the muscles to repeatedly contract and relax and consequently grow and increase in strength to lessen urinary incontinence.

11. A method according to claim 10 wherein stress incontinence is to be treated and said electrical pulses have a peak current in the range of from about 10 to about 100 milliamps and a frequency in the range of from about 40 to about 60 Hz and are applied in pulses lasting from about 5 to about 10 seconds with an interval between pulses in the range of from about 5 to about 10 seconds.

12. A method according to claim 11 wherein said electric pulses have a peak current of about 40 milliamps and a frequency of about 50 Hz and are applied as pulses lasting for about 5 seconds with an interval between pulses in the range of from about 5 to about 10 seconds.

13. A method according to claim 10 wherein urge incontinence is to be treated and the electric pulses have a peak current in the range of from about 10 to about 100 milliamps and a frequency in the range of from about 10 to about 15 Hz and are applied as pulses lasting from about 5 to about 10 seconds with an interval between pulses in the range of from about 5 to about 10 seconds.

14. A method according to claim 13 wherein said electric impulses have a peak current of about 40 milliamps and a frequency of about 13 Hz and are applied as pulses lasting for about 5 seconds with an interval between pulses in the range of from about 5 to about 10 seconds.

* * * * *